US012635971B2

(12) United States Patent
Tanter et al.

(10) Patent No.: US 12,635,971 B2
(45) Date of Patent: May 26, 2026

(54) METHOD AND APPARATUS FOR IMAGING VASCULAR ACTIVITY DYNAMICALLY AT A MICROSCOPIC SCALE

(71) Applicants: INSTITUT NATIONAL DE LA SANTÉ ET DE LA RECHERCHE MÉDICALE, Paris (FR); CENTRE NATIONAL DE LA RECHERCHE SCIENTIFIQUE, Paris (FR); ECOLE SUPÉRIEURE DE PHYSIQUE ET DE CHIMIE INDUSTRIELLES DE LA VILLE DE PARIS, Paris (FR)

(72) Inventors: Mickael Tanter, Paris (FR); Thomas Deffieux, Paris (FR); Noémi Renaudin, Paris (FR); Charlie Demené, Paris (FR)

(73) Assignees: INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); ECOLE SUPÉRIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 0 days.

(21) Appl. No.: 18/728,714

(22) PCT Filed: Feb. 17, 2023

(86) PCT No.: PCT/EP2023/053992
§ 371 (c)(1),
(2) Date: Jul. 12, 2024

(87) PCT Pub. No.: WO2023/156576
PCT Pub. Date: Aug. 24, 2023

(65) Prior Publication Data
US 2025/0099070 A1 Mar. 27, 2025

(30) Foreign Application Priority Data

Feb. 18, 2022 (EP) ..................................... 22305183

(51) Int. Cl.
$A61B\ 8/08$ (2006.01)
$A61B\ 8/00$ (2006.01)
(Continued)

(52) U.S. Cl.
CPC ............ *A61B 8/0808* (2013.01); *A61B 8/481* (2013.01); *A61B 8/5246* (2013.01); *A61B 8/54* (2013.01); *A61B 8/04* (2013.01); *A61B 8/06* (2013.01)

(58) Field of Classification Search
CPC .... A61B 8/06; A61B 8/04; A61B 8/54; A61B 8/481; A61B 8/5246; A61B 8/0808
See application file for complete search history.

(56) References Cited

U.S. PATENT DOCUMENTS

| | | | |
|---|---|---|---|
| 2008/0119727 A1* | 5/2008 | Barbagli | A61B 90/36 600/437 |
| 2013/0094729 A1* | 4/2013 | Mauldin, Jr. | A61B 8/5207 382/128 |

(Continued)

OTHER PUBLICATIONS

Errico et al.; "Ultrafast ultrasound localization microscopy for deep super-resolution vascular imaging", vol. 527; Nature ; pp. 499-507 (Year: 2015).*

(Continued)

*Primary Examiner* — Dixomara Vargas
(74) *Attorney, Agent, or Firm* — WCF IP

(57) ABSTRACT

Method for imaging vascular activity dynamically at a microscopic scale in a vascular network of a human or animal, the method including: (a) performing a temporal series of Ultrasound Localization Microscopy images of a region of the vascular network, to obtain values of a vascular
(Continued)

dynamics parameter in an area of interest in the region, a recording period of the temporal series of ULM images corresponding to a dynamical event, due to a cause other than cardiac pulsatily, which activates the vascular network in the region; (b) computing, based on the values of the vascular dynamics parameter, a measure of an evolution of the vascular dynamics parameter in response to the dynamical event.

21 Claims, 7 Drawing Sheets

(51) Int. Cl.
A61B 8/04          (2006.01)
A61B 8/06          (2006.01)

(56)                    References Cited

U.S. PATENT DOCUMENTS

| 2016/0247325 | A1* | 8/2016 | Yu | A61B 6/4476 |
| 2020/0008779 | A1* | 1/2020 | Göksel | G01S 15/8993 |
| 2021/0244374 | A1* | 8/2021 | Zhao | A61B 6/4241 |
| 2023/0239583 | A1* | 7/2023 | Vercauteren | G01J 3/0264 |
| | | | | 348/273 |
| 2023/0301623 | A1* | 9/2023 | Cormier | A61B 8/488 |
| 2024/0269489 | A1* | 8/2024 | Kvåle | A61N 7/00 |

OTHER PUBLICATIONS

Foiret et al.; "Ultrasound localization microscopy to image and assess microvasculature in a rat kidney"; Scientific Reports | 7: 13662 | DOI:10.1038/s41598-017-13676-7; pp. 1-12 (Year: 2017).*
Couture et al.; "Ultrasound Localization Microscopy and Super-Resolution: A State of the Art"; IEEE Transactions on Ultrasonics, Ferroelectrics, and Frequency Control, vol. 65, No. 8, Aug. 2018; pp. 1304-1320 (Year: 2018).*
Yan et al. ; "Transthoracic ultrasound localization microscopy of myocardial vasculature in patients"; Nature Biomedical Engineering | vol. 8 | Jun. 2024 | 689-700 (Year: 2024).*
Dencks et al. ; "Ultrasound localization microscopy"; S. Dencks, G. Schmitz / Z Med Phys 33 (2023) 292-308 (Year: 2023).*
Liu et al.; "Deep Learning for Ultrasound Localization Microscopy"; IEEE Transactions on Medical Imaging, vol. 39, No. 10, Oct. 2020; pp. 3064-3078 (Year: 2020).*
Qian et al.; "Super-Resolution Ultrasound Localization Microscopy for Visualization of the Ocular Blood Flow"; IEEE Transactions on Biomedical Engineering, vol. 69, No. 5, May 2022; pp. 1585-1594 (Year: 2022).*
Labastida-Ramirez et al. ; "State-of-the-art preclinical techniques to study the impact of spreading depolarizations in awake rodents"; The Journal of Headache and Pain (2025) 26:188 (Year: 2025).*
Andrew K. Dunn; "Laser Speckle Contrast Imaging of Cerebral Blood Flow"; Annals of Biomedical Engineering, vol. 40, No. 2, Feb. 2012 ( 2011) pp. 367-377 (Year: 2012).*
Andersen et al: "Super-Resolution Ultrasound Imaging of Rat Kidneys before and after Ischemia-Reperfusion", 2019 IEEE International Ultrasonics Symposium (IUS), p. 1169-1172, Oct. 6, 2019.
Deffieux et al: "Functional Ultrasound Imaging: A New Imaging Modality for Neuroscience", Neuroscience, vol. 474, p. 110-121, Mar. 13, 2021.
Errico et al: "Transactional functional ultrasound imaging of the brain using microbubble-enhanced ultrasensitive Doppler", Neuroimage, vol. 124, p. 752-761, Jan. 1, 2016.

* cited by examiner

METHOD AND APPARATUS FOR IMAGING VASCULAR ACTIVITY DYNAMICALLY AT A MICROSCOPIC SCALE

TECHNICAL FIELD

The present disclosure concerns methods and apparatuses for imaging vascular activity dynamically at microscopic scale in a human or animal.

BACKGROUND ART

Most brain-wide functional imaging modalities exploit neurovascular coupling to map brain activity in millimetric resolutions. More specifically, activated zones of the nervous system need more oxygen, thus locally increasing the flow of blood in the vascular network of said nervous system, in particular in the capillaries, venules and arterioles of the vascular network. Hence, the nervous activity in the nervous system may be estimated, at a millimetric scale, based on the activity of the vascular network in said nervous system.

Nevertheless, the recording of functional responses at a microscopic scale in mammals remains the privilege of electrophysiological or optical approaches. However, the electrophysiological and optical approaches are restricted to either the cortical surface or the immediate vicinity of implanted sensors.

That is, functional imaging is limited by either a spatial resolution, in the case of neurovascular coupling-based methods, or by a penetration depth, in the case of electrophysiological and optical methods.

One type of imaging of high interest, particularly regarding spatial resolution and penetration depth, is Ultrasound Localization Microscopy (ULM), which has been described in particular by Errico et al. [Errico, C. et al. Ultrafast ultrasound localization microscopy for deep super-resolution vascular imaging. *Nature* 527, 499-+ (2015)] and Demene et al. [Demene, C. et al. Transcranial ultrafast ultrasound localization microscopy of brain vasculature in patients. *Nat. Biomed. Eng* 5, 219-228 (2021)]. Ultrasound Localization Microscopy achieves transcranial imaging of cerebrovascular flow, up to micron scale, by localizing millions of intravenously injected microbubbles (MB). However, as described by Hingot et al. [Hingot, V. et al. Microvascular flow dictates the compromise between sensitivity to tiny vessels and acquisition time in Ultrasound Localization Microscopy. *Scientific Reports* 9, (2019)], within microscopic vessels, the long acquisition time required to detect single microbubble signatures has so far restricted ULM application mainly to microvasculature structural imaging.

Therefore, there exists a need for imaging vascular activity, in particular brain-wide vascular activity, dynamically at a microscopic scale.

SUMMARY

To this end, the present disclosure proposes a method for imaging vascular activity dynamically at a microscopic scale in a vascular network, preferably of a nervous system, of a human or animal, the method including:

(a) performing a temporal series of Ultrasound Localization Microscopy (ULM) images of at least one region of the vascular network, to obtain values of at least one vascular dynamics parameter in at least one area of interest in the at least one region during a recording period, the temporal series of ULM images being constructed from a temporal series of images of the region, each ULM image being constructed from a stack of images of the temporal series of images, at least some of the images of a stack of images corresponding to a $(k+1)^{th}$ ULM image having a time position superior to that of the images of a stack of images corresponding to a $k^{th}$ ULM image which is immediately preceding the $(k+1)^{th}$ ULM image, said recording period of the temporal series of ULM images including at least one dynamical event, due to a cause other than cardiac pulsatility, the dynamical event activating a change in an hemodynamics and/or a change in a structural conformation of the vascular network in the at least one region thereof;

(b) computing, based on the values of the at least one vascular dynamics parameter from the temporal series of ULM images, a measure of an evolution of the at least one vascular dynamics parameter in response to the dynamical event.

The proposed method advantageously allows, depending on the embodiment, to obtain a dynamic understanding of the vascular activity at a microscopic scale. Owing to the collection of the temporal series of individual ULM images, information from the individual ULM images may be gathered. The gathering of information from the individual ULM images may reduce the acquisition period of the individual ULM images, while maintaining a high spatial resolution. In some embodiments, the acquisition period for the temporal series may hence be inferior to the theoretical limiting acquisition period disclosed by Hingot et al. [Hingot, V. et al. Microvascular flow dictates the compromise between spatial resolution and acquisition time in Ultrasound Localization Microscopy. *Scientific Reports* 9, (2019)]. The three-dimensional (3D) information from the temporal series of individual ULM images allows to derive a measure of an evolution of the at least one vascular dynamics parameter in response to the dynamical event.

In some embodiments, the present inventors achieved to study functional hyperemia, which is an increase of blood flow to different tissues in the body, dynamically during brain activation. Notably, in some embodiments, the inventors achieved a spatiotemporal resolution of (6.5 µm, 1 s) in deep cortical and subcortical regions of the rat brain, surpassing the "classic" ULM performances limited by long acquisition periods. That is, quantitative information on both the function and dysfunction of living organs may be obtained.

In one embodiment, each image of the temporal series of images may be constructed from successive compound images. Each compound image of the region may be obtained from a set of transmitted planar or diverging ultrasonic waves from the region.

In one embodiment, the vascular network has been previously administrated with ultrasound contrast agents before acquiring the images.

The following features, can be optionally implemented, separately or in combination one with the others:

In one or more embodiments, the vascular network may be a vascular network of a nervous system and the at least one dynamical event may be a stimulus delivered to the nervous system. The method may further include:

(c) delivering the at least one stimulus to the nervous system.

The measure of the evolution of the at least one dynamics parameter computed from the temporal series of ULM images may reflect a response of the at least one region of the nervous system to the at least one stimulus. In some embodiments, brain-wide vascular activity may hence be measured during task-evoked activity. Additionally, in some embodiments, the spatial extent and influence of the at least one region of the nervous system may be deciphered during task-evoked activity.

In one or more embodiments, the vascular network may be a vascular network of a nervous system and the at least one dynamical event may be a spontaneous activity of the nervous system.

The measure of the evolution of the at least one dynamics parameter computed from the temporal series of ULM images may reflect a functional connectivity of the at least one region of the nervous system. In some embodiments, it may hence be possible to measure interactions occurring in the brain in a resting or task-negative state.

In one or more embodiments, a recording period of an ULM image of the temporal series of ULM images may be superior to a period of a cardiac cycle and inferior to a minute.

The recording period for an ULM image may hence be reduced with respect to a "classic" ULM image, while being sufficiently long to observe ULM contrast agents.

In one or more embodiments, steps (a) and (c) may be repeated for N trials and the evolution of the at least one vascular dynamics parameter may be computed based on the temporal series of the n trials, n being an integer larger than 1.

In some embodiments, the information for computing measure of the evolution of the at least one vascular dynamics parameter may be enriched by repeating a stimulus' pattern during the n trials and combining equivalent time points in the n trials. A sparsity of the information for computing the measure of the evolution of the at least one vascular dynamics parameter may hence be reduced. A sensitivity of the information for computing the evolution of the at least one vascular dynamics parameter may be increased.

In one or more embodiments, the computation of the measure of the evolution of the at least one vascular dynamics parameter in response to the dynamical event may comprise a correlation analysis between the stimulus and the temporal series of ULM images.

The correlation analysis between the stimulus and the temporal series of ULM images may provide a quantitative map of functional hyperemia.

In one or more embodiments, the computation of the measure of the evolution of the at least one vascular dynamics parameter in response to the dynamical event may comprise a more sophisticated processing analysis, comprising but not restricted to, Singular Value Decomposition (SVD) or a Principal Component Analysis (PCA), of the temporal series of ULM images.

The processing analysis of the temporal series of ULM images may allow to isolate the measure of the evolution of the at least one vascular dynamics parameter in response to the dynamical event from an ultrasound agent injection's profile. The evolution of the at least one vascular dynamics parameter in response to the dynamical event may hence be observed independently of the ultrasound agent injection's profile. For instance, the SVD of the temporal series of ULM images may allow to isolate functional hyperemia in one singular vector (and the ultrasound agent injection's profile in another singular vector). Local variations of the contrast agents of the ULM method may be represented in singular vectors of the SVD. A quantitative map of functional hyperemia may hence be obtained.

In one or more embodiments, the computation of the measure of the evolution of the at least one vascular dynamics parameter in response to the dynamical event may comprise a sliding average of the temporal series of ULM images.

Performing the sliding average of the temporal series of ULM images may allow to observe a smoothed evolution of the brain activity. In particular, for diffusive or propagative events, such as epileptic seizures or spreading depressions, an analysis of the diffusion or the propagation of the seizure or spreading depression may be obtained.

In one or more embodiments, successive ULM images of the temporal series of ULM images may be obtained from stacks of images that at least partially overlap.

Computing the consecutive ULM images of the temporal series of ULM images based on stacks of images that at least partially overlap in the temporal dimension may increase the temporal resolution of the measure of the at least one vascular dynamics parameter.

In one or more embodiments, successive ULM images of the temporal series of ULM images may be obtained from respective stacks of images that are successive in the temporal dimension.

In some embodiments, said respective stacks of images may be immediately adjacent in the temporal dimension.

In one or more embodiments, the at least one vascular dynamics parameter computed may be chosen in the group comprising: blood flow, blood velocity, blood volume, blood pressure, vascular vessels' diameters, and any combination thereof.

Computing a dynamics parameter among blood flow, blood velocity, blood volume, blood pressure, vascular vessels' diameters, and any combination thereof may allow to derive a behavior of the at least one region of the vascular network, enabling to quantify the activity of the at least one region without requiring a large amount of information from different types. The diameter may be obtained by different segmentation techniques applied to the ULM images. In its simplest form, it could be defined as a width of the vessel at a threshold set by the Half Maximum of a rest profile. Blood flow may be derived from a ULM contrast agents' flow during a recording of the temporal series. Blood velocity may be derived from a ULM contrast agents' velocity during a recording of the temporal series.

In one or more embodiments, the region may be further segmented in one or more vascular compartments such as penetrating arterioles, pial vessels, intraparenchymal vessels or venules and the at least one area of interest may be corresponded to at least one of said vascular compartment.

The present disclosure also concerns an apparatus for imaging vascular activity dynamically at a microscopic scale in a vascular network, preferably of a nervous system, of a human or animal, the apparatus including:

(a) an ultrasound contrast agent injection device and an ultrasound measuring device adapted to perform a temporal series of Ultrasound Localization Microscopy, ULM, images of at least one region of the vascular network, to obtain values of at least one vascular dynamics parameter in at least one area of interest in the at least one region during a recording period, the temporal series of ULM images being constructed from a temporal series of images of the region, each ULM image being constructed from a stack of images of the temporal series of images, at least some of the images of a stack of images corresponding to a $(k+1)^{th}$ ULM image having a time position superior to that of the images of a stack of images corresponding to a k$^{th}$ ULM image which is immediately preceding the (k+1)$^{th}$ ULM image, said recording period of the temporal series of ULM images including at least one dynamical event, due to a cause other than cardiac pulsatility, the dynamical event activating a change in an hemodynamics and/or a change in a structural conformation of the vascular network in the at least one region thereof;

(b) a computing module adapted to compute, based on the values of the at least one vascular dynamics parameter from the temporal series of ULM images, a measure of an evolution of the at least one vascular dynamics parameter in response to the dynamical event.

In embodiments of the apparatus, one may use the following features, alone or in combination:

In one or more embodiments, the dynamical event may be an epileptic seizure or a spreading depression and the computing module may be adapted to estimate a seizure focus location or a spreading depression origin from the measure of the evolution of the at least one vascular dynamics parameter in response to the epileptic seizure or the spreading depression.

The measure of the evolution of the vascular dynamics parameter of the region of the vascular network may allow to track the dynamics of the brain activity. In some embodiments, the focus location of the epileptic seizure occurring during the recording of the temporal series may be identified by examining the evolution of the brain activity. For example, in some embodiments, by analyzing the flow's direction and/or the velocity, the epileptic focus may be identified. Hence, the object of the present description, by its spatiotemporal resolution, may allow a precise and rapid identification of the epileptic focus. Similarly, the spreading depression origin may be precisely and rapidly identified.

In one or more embodiments, the computing module may be adapted to diagnosticate whether the measure of the evolution of the at least one vascular dynamics parameter in response to the dynamical event corresponds to a predetermined disease, in particular a neurodegenerative disease.

In some embodiments, the object of the present description may allow to map brain-wide functional activity, offering insights on neural brain circuits. The measure of the evolution of the at least one vascular dynamics parameter in response to the dynamical event may be compared to a predetermined threshold (in case of several vascular dynamics parameters: respectively comparing each response parameter to a corresponding predetermined threshold) characterizing whether the measure of the evolution of the vascular dynamics parameter is normal and/or whether the vascular dynamics parameter corresponds to a predetermined disease.

In one or more embodiments, the computing device is adapted to monitor efficiency of a medical treatment against a predetermined disease; in particular a disease among epilepsy, spreading depression and a neurodegenerative disease, based on the measure of the evolution of the at least one vascular dynamics parameter in response to the dynamical event.

Evolution of the vascular dynamics parameter in response to the medical treatment may allow to efficiently monitor the impact of the medical treatment. Adaptation of the medical treatment may be derived of the monitoring thereof.

In another aspect, it is proposed a computer software comprising instructions to implement at least a part of a method as defined here when the software is executed by a processor. In another aspect, it is proposed a computer-readable non-transient recording medium on which a software is registered to implement the method as defined here when the software is executed by a processor.

BRIEF DESCRIPTION OF DRAWINGS

Other features, details and advantages will be shown in the following detailed description and on the figures, on which:

FIG. 6(*b*) shows an example of a measure (activation map) of an evolution of at least one vascular dynamics parameter in response to a dynamical event in a rat obtained with a functional Ultrasound (fUS method).

FIG. 7(*b*) shows dynamic histograms of the microbubbles velocity distribution in the compartments defined in FIG. 7(*a*).

DESCRIPTION OF EMBODIMENTS

In the Figures, the same references denote identical or similar elements.

The present disclosure proposes a method and apparatus for imaging vascular activity dynamically at a microscopic scale in a vascular network, preferably of a nervous system, of a human or animal, by performing a temporal series of Ultrasound Localization Microscopy images of at least one region of the vascular network. A recording period of the temporal series of ULM images may include at least one dynamical event, which is due to a cause other than cardiac pulsatility. The at least one dynamical event may be due to a neuronal or other cells activity. The at least one dynamical event may be provoked, such as a task-evoked stimulus, or not, such as a spontaneous activity, a seizure or a spreading depression. The temporal series of ULM images enables to obtain values of at least one vascular dynamics parameter in at least one area of interest in the at least one region. Based on the values of the at least one vascular dynamics parameter from the temporal series of ULM images, a measure of an evolution of the at least one vascular dynamics parameter in response to the dynamical event may be computed.

The region of the vascular network may be a brain slice for 2D imaging or a 3D region of the brain for 3D imaging.

In some embodiments, ULM images may be obtained based on methods already known in the art and explained in the above articles of Errico et al., 2015 and Demene et al., 2021.

Figure 1:
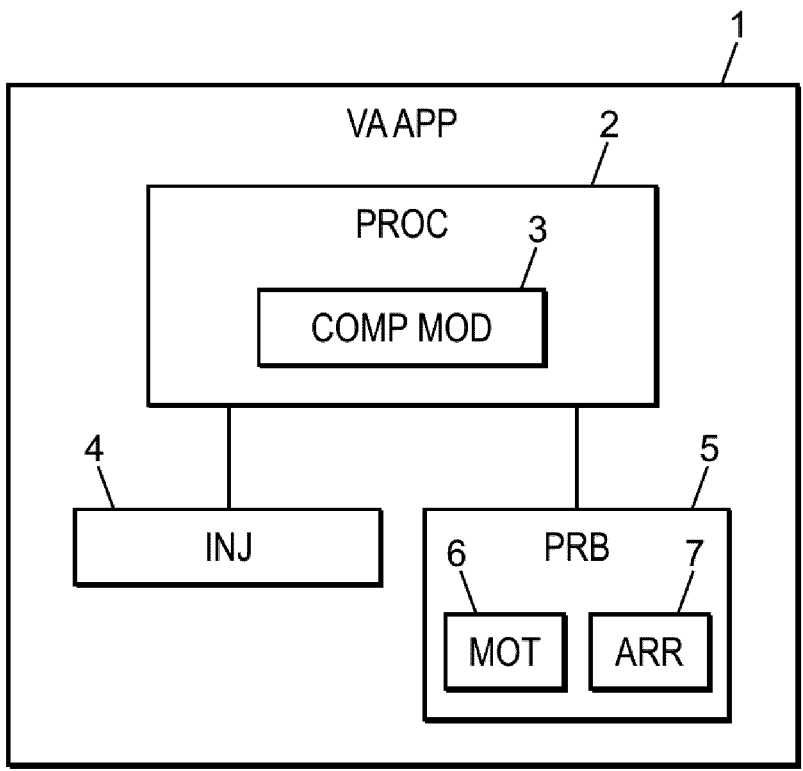
FIG. 1 is a block diagram illustrating an embodiment of an apparatus according to the present disclosure.

An example of apparatus 1 (VA APP) for imaging vascular activity usable in performing the method according to the present disclosure, is shown on FIG. 1.

The apparatus 1 may include a processor 2 (PROC), for instance a specialized signal processing device controlled by a computer or a group of computers, possibly a group of computers including servers.

The processor 2 may include a computing module 3 (COMP), the operation of which will be explained later.

The processor 2 may control an ultrasound contrast agent injection device 4 (INJ).

The ultrasound contrast agent injection device 4 may comprise ultrasound contrast agents. The ultrasound contrast agents may be microbubbles, as for instance described by Dayton et al., [Dayton, P A et al. Molecular ultrasound imaging using microbubble contrast agent. *Frontiers in Bioscience* 12, 5124-5142 (2007)], or equivalent ultrasound contrast agents. In some embodiments, the ultrasound contrast agents may be based on SonoVue®.

The ultrasound agent injection device 4 may be a push syringe in the example considered here.

The ultrasound agent injection device 4 may comprise a magnet in order to mix a solution comprising the ultrasound contrast agents.

The processor 2 may control a probe 5 (PRB).

The probe 5 may be for instance an ultrasonic probe in the example considered here.

The probe 5 may include an array 7 (ARR) of ultrasonic transducers. The array may be a linear array adapted to generate a 2D image of a slice of the region to be imaged, or a 2D array adapted to generate a 3D image of the region. When the array is a 2D array, it may be a sparse matrix of transducers, as known in the art.

Typical arrays of transducers may include a few hundreds to a few thousand of transducers. The array may also in some examples, be limited to one single transducer adapted to image only one line of the region, in the direction of the depth from the transducer or a few transducers adapted to image respectively lines of the region, in the direction of the depth from the transducer.

The following detailed description is done for the case of a linear or 2D array, so that the apparatus generates ultrasound measurements having pixels. In the case where the array would include just one transducer or a few transducers, the apparatus would generate an image limited to one line (ultrasound measurement) or a few lines in the direction of depth, the line(s) having pixels and the process would be similar except for the generation of the ultrasound measurements which would not require inclined planar waves of different angles of inclination.

The transducer(s) may be adapted to transmit and receive ultrasound waves having a central frequency comprised for instance between 0.5 and 100 MHz, for instance between 1 and 20 MHz. One example of usable central frequency is 15 MHz.

In certain embodiments, the probe 5 may further include a motorization 6 (MOT) adapted to position the array 7.

In some embodiments, the processor 2 may additionally control a stimulating device, which is not represented on FIG. 1.

Figure 2:
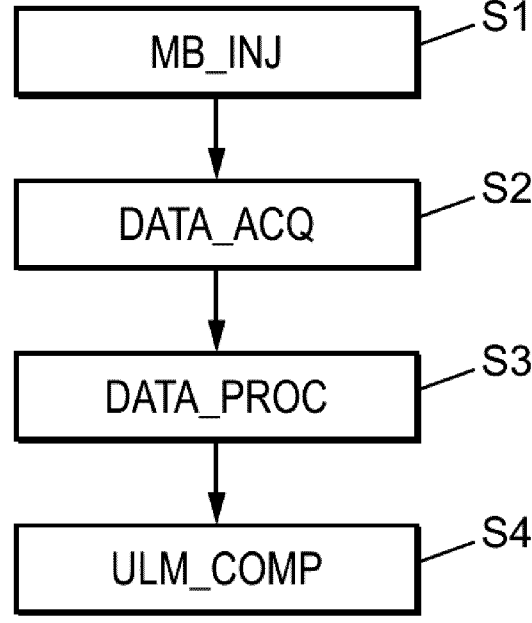
FIG. 2 is a block diagram illustrating a possible method of obtaining an ULM image with the apparatus of FIG. 1.

An example of method of Ultrasound Localization Microscopy imaging, already known in the art and explained for instance in the above article of Demene et al., 2021, will now be explained with regards to FIG. 2 and FIG. 3.

The ultrasound contrast agent injection device 4 may be controlled by the processor 2 to inject S1 (MB_INJ) intravenously ultrasound contrast agents to a region of the vascular network.

The ultrasound contrast agent injection may be a bolus injection with a maximum injection volume of 40 ml/kg for rats (corresponding to 12 mL for a 300 g rat and approximately 3 mL for a 70 g mice) and a typical 6 mL injection volume for rats and 2 mL injection volume for mice. For a human, a maximum volume of 10 mL may be injected. For instance, two bolus of 2.4 mL may be injected in the human.

The ultrasound contrast agent injection may be a continuous injection. For instance, a flow rate of the continuous injection may be comprised between 3 mL/h/kg and 60 mL/h/kg, and preferably approximatively 10 mL/h/kg (or typically 3.5 mL/h for a 300 g rat and 1.0 mL/h for a 70 g mice).

The array 7 of transducers may be controlled by the processor 2 to acquire S2 (DATA_ACQ) compound images of the region during the ultrasound contrast agent injection.

In one embodiment, the array of transducers may acquire compound images of the region of the vascular network that has been previously administrated with ultrasound contrast agents.

The computing device 3 may process S3 (DATA_PROC) the acquired compound images of the region to obtain filtered images of the region.

The computing module 3 may compute S4 (ULM_COMP) ULM images of the region of the vascular network based on the filtered images of the regions.

Figure 3:
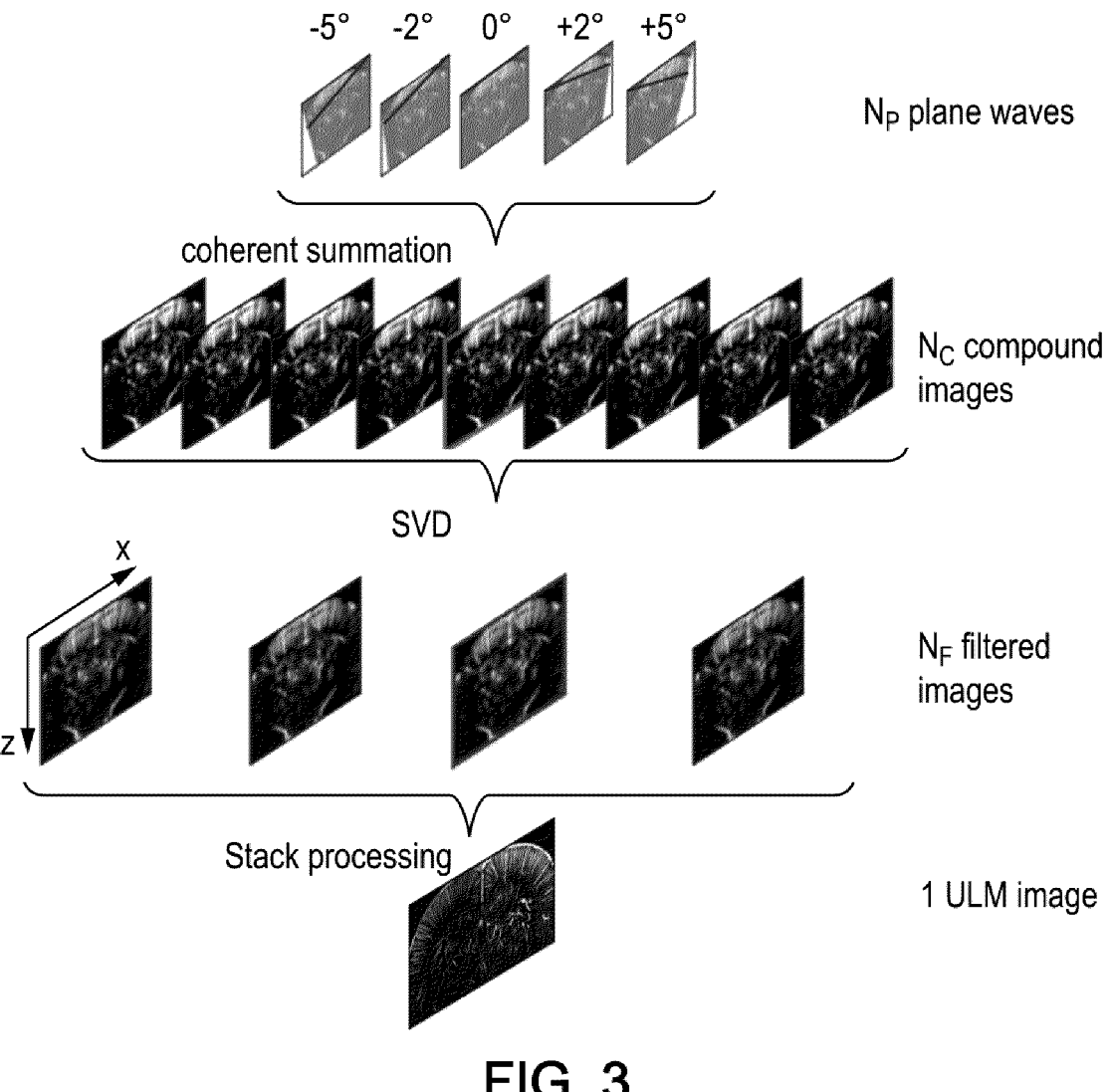
FIG. 3 illustrates a possible method of obtaining an ULM image with the apparatus of FIG. 1.

In the example of FIG. 3, the array 7 of transducers may be controlled by the processor 2 to acquire S2 compound images of the region during the ultrasound contrast agent injection by transmitting planar ultrasonic waves in the region to be imaged and by receiving the resulting backscattered ultrasonic waves, at a rate of for instance 5 kHz (Pulse Repetition Frequency PRF), i.e. every 0.2 ms. More generally, the Pulse Repetition Frequency PRF may be over 500 Hz. The received signals may be registered as a set of raw data for each transmitted planar ultrasonic wave. The successive transmitted planar waves may have propagation directions which are inclined of varying successive angles with regards to the direction of the depth in the region to be imaged, i.e. with regards to the direction normal to the array 7. For each image of the region, a number $N_p$ of planar ultrasonic waves may be successively transmitted with different angles and the N sets of raw data may be coherently added to synthesize said image of the region, which is thus a compound image. For instance, $N_p$ may be 5 with angles taking the values −5 deg, −2 deg, 0 deg, +2 deg, +5 deg. In the case of $N_p$=5 and PRF=5 kHz, the rate of the compound images of the region (framerate) is thus 1 kHz. $N_p$ may be different than 5, in which case the framerate of compound images is different. For instance, $N_p$=11 may be used. The array 7 of transducers may be placed on a skull of a human or animal for transcranial experiments, or directly on a brain of the human or animal for experiments involving a craniotomy.

Based on the successive compound images of the region, filtered images of the vascular network in said region may then be computed S3 by the computing module 3. In the example of FIG. 3, $N_c$ successive compound images are used for each filtered image. The $N_c$ successive compound images may be temporally continuous or may partially overlap in the temporal dimension. For instance, $N_c$ may be comprised between 10 and 1000, for instance between 200 and 600. One example of usable number of successive compound images for one filtered image is 400. Time positions may be associated to the filtered images. A time position for a given filtered image may correspond to an average of acquisition times of the Nc compound images forming the filtered image.

The filtered images may be computed for instance by a Singular Value Decomposition (SVD). More specifically, a SVD spatiotemporal clutter filter, as for instance described by Demene et al. [Demene, C. et al. Spatiotemporal Clutter Filtering of Ultrafast Ultrasound Data Highly Increases Doppler and fUltrasound Sensitivity. *IEEE Transactions on Medical Imaging* 34, 2271-2285 (2015)], may be applied. In the example of FIG. 3, each filtered image may be a singular value or a sum of singular values of the SVD applied to the $N_c$ compound images. In some embodiments, an ultrasonic signature of the individual ultrasound contrast agents may be discriminated from a tissue signal, due to cardiac and breathing pulsatility, of the region by performing a speckle tracking correlation analysis of the compound images prior to applying the SVD, as described by Hingot et al. [Hingot, V. et al. Subwavelength motion-correction for ultrafast ultrasound localization microscopy. *Ultrasonics* 77, 17-21 (2017)]. Alternatively, owing to the SVD of the compound images, for each filtered image, the ultrasonic signature of the individual ultrasound contrast agents may be discriminated from the tissue signal of the region. By discarding some singular values of the SVD, the tissue signal may be filtered. For instance, the first 10 singular values of the SVD, mostly reflecting the tissue signal of the region, may be discarded.

Each of the filtered images may be interpolated. For instance, each of the filtered images may be interpolated by a Lanczos interpolation kernel. Each of the filtered images may be interpolated to achieve a sampling rate in the order of $(\alpha/6\times\varepsilon/6)$, where $\alpha$ is a spatial pitch of the probe and $\varepsilon$ is a wavelength of the ultrasounds.

A stack of the filtered images may be filtered based on a vesselness filtering, as for instance described by Jerman et al. [Jerman, T. et al. Enhancement of Vascular Structures in 3D and 2D Angiographic Images. *IEEE Transactions on Medical Imaging* 35, 2107-2118 (2016)].

Ultrasound contrast agents may be detected in the filtered images. For instance, ultrasound contrast agents may be detected as the brightest local maxima with high correlation with a point spread function. High correlation may be defined as a correlation superior to a threshold. The threshold may be a value comprised between 0.5 and 1. For instance, the threshold may be equal to 0.7. The point spread function is an imaging response of an isolated ultrasound contrast agent, which may be modelled as a Gaussian spot of axial and lateral dimension of $\varepsilon$. Sub-pixel maxima localization may be performed using a fast local second-order polynomial fit. A neighborhood for the fast local second-order polynomial fit may be a 5×5 pixel neighborhood. Coordinates of the localized sub-pixel maxima may be rounded to a chosen pixel size. The chosen pixel size may be inferior to the pixel size of the filtered image. For instance, the chosen pixel size may be a submultiple of the pixel size of the filtered image. The submultiple may be a multiple of 2. For instance, the submultiple may be equal to 16.

Ultrasound contrast agents may be tracked in the filtered images. A tracking of the ultrasound contrast agents may be performed using a particle tracking algorithm known in the art. Tracks may be computed based on the tracking of the ultrasound contrast agents in the filtered images. A track may correspond to positions of a tracked ultrasound contrast agent in the filtered images. Each position of a tracked ultrasound contrast agent in the filtered images may be associated with a time position corresponding to the time position of the filtered image in which the position is located. Tracks with ultrasound contrast agents detected in a predefined number of successive filtered images may be computed. The predefined number of successive filtered images may be comprised between 1 and 100. For instance, the predefined number of successive filtered images may be 10. A spatial interpolation may be computed for each track in order to obtain one ultrasound contrast agent in each pixel located on the path between two successive pixels of the track.

Successive positions of ultrasound contrast agents in a track may be used to compute velocity parameters. For example, interframe ultrasound contrast agent velocity vector components (along a probe x-axis and a depth z-axis for 2D imaging and along a probe x-axis, y-axis and a depth z-axis for 3D imaging) may be computed. Absolute velocity magnitude may be computed.

Based on the filtered images, the ULM images may be computed S4 (ULM_COMP) by the computing module 3. The ULM images may be computed based on the tracks, which are based on the filtered images. In the example of FIG. 3, $N_F$ filtered images are used for each ULM image. Each ULM image may be constructed by selecting a pixel size and by sorting each detected ultrasound contrast agent of the $N_F$ filtered images within each pixel. In some embodiments, values of pixels accumulating a value of detected ultrasound contrast agents in the $N_F$ filtered images inferior to a threshold are set to zero. The threshold may be comprised between 1 and 10, preferably 5.

ULM images of ultrasound contrast agent count may be computed based on the detected ultrasound contrast agents. For instance, ULM count images may be computed by counting, for each pixel, the number of ultrasound contrast agents detected in the corresponding pixel of the filtered images. In the example of FIG. 3, for each pixel, the number of ultrasound contrast agents detected in the corresponding pixel of the $N_F$ filtered images may be used.

ULM velocity images of the ultrasound contrast agent velocity may be computed based on the detected ultrasound contrast agents. For instance, velocity maps may be computed based on the interframe ultrasound contrast agent velocity vector components and/or the absolute velocity magnitude.

A slow-motion drift may occur in the ULM images potentially due to recording periods superior to a period of the cardiac cycle and to a period of the breathing cycle. The slow-motion drift may also result from an anesthesia in anesthetized humans or animals. In cases where a craniotomy is performed, potential brain swelling of the brain may contribute to the slow-motion drift. A correction of the slow-motion drift may be performed via an intensity-based spatial registration. The intensity-based spatial registration may be one of a translation transformation, a translation and a rotation transformation or a more complex non rigid transformation. The intensity-based spatial registration may be performed based on a ULM image of a period inferior to the recording period. For instance, a 10 s ULM count image may be used to correct the drift occurring in the ULM images of a larger recording period. Correction of the slow-motion drift may enable to observe the dynamical event object of the present disclosure, which is due to a cause other than cardiac pulsatility and which may be slower than the cardiac pulsatility (for instance, the dynamical event may correspond to neural activity and/or an inflammatory response)

Figure 4:
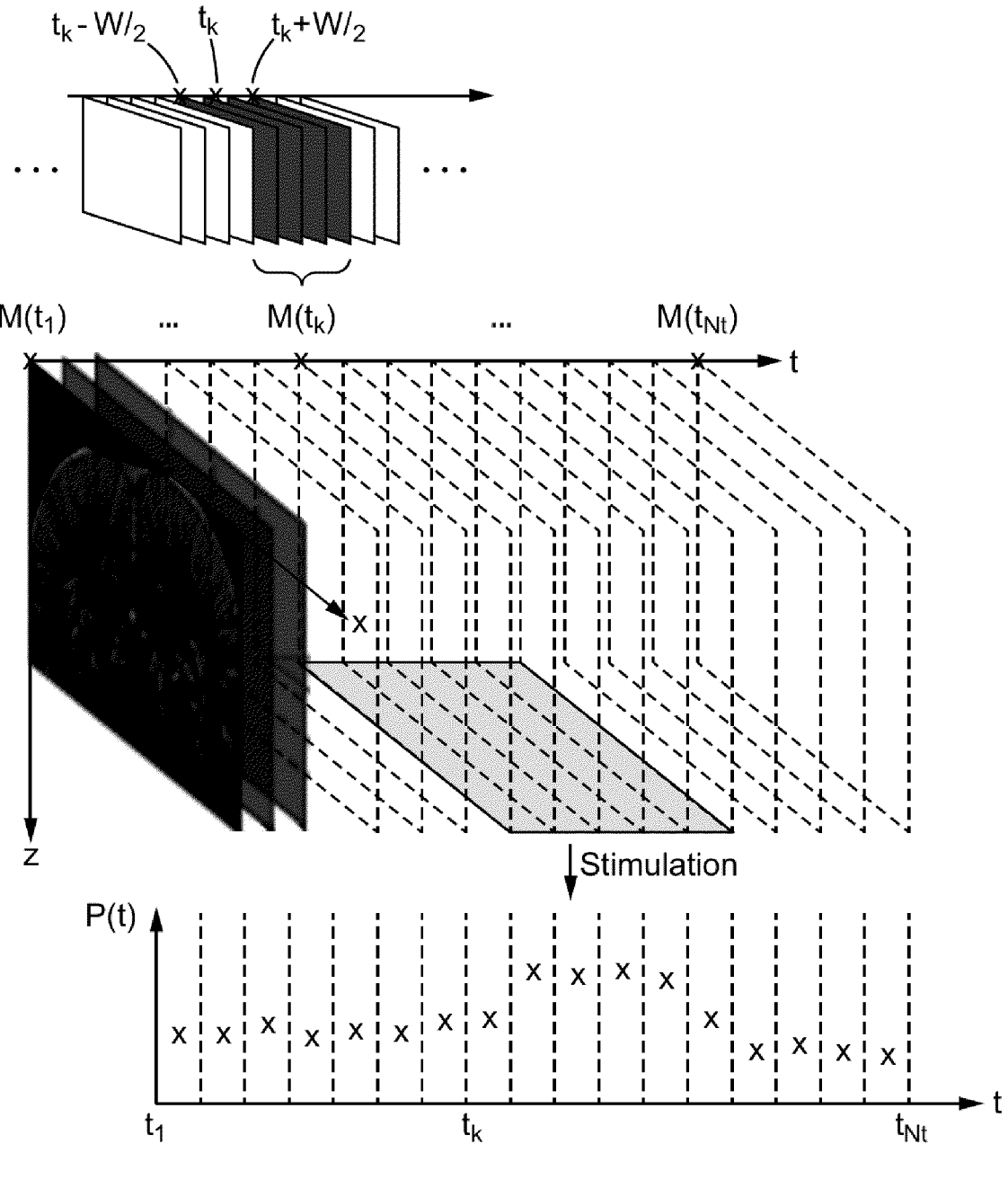
FIG. 4 illustrates a possible method of computing at least a measure of an evolution of at least one vascular dynamics parameter in response to a dynamical event according to an embodiment of the present invention.

FIG. 4 illustrates how a temporal series of ULM images of the region may be created.

Instead of using the whole acquisition dataset, that is the $N_F$ filtered images, to compute a unique ULM count image or a unique velocity image, as known in the prior art, a temporal series of successive ULM images of the region may be derived from the acquisition dataset. A recording period of the acquisition dataset includes at least one dynamical event. The dynamical event activates the vascular network in the at least one region imaged. Each $N_F$ filtered image is constructed from successive compound images $N_c$ transmitted from the region. The whole acquisition dataset forms a temporal series of filtered images. Each filtered image is associated with a time position in the recording period. The temporal series of filtered images may be used to form a temporal series of stacks of filtered images. Each ULM image of the temporal series of successive ULM is associated with a time position in the recording period. Each ULM image may be constructed from a stack of filtered images of the temporal series of images, at least some of the images of a stack of images corresponding to a $(k+1)^{th}$ ULM image having a time position superior to that of the images of a stack of images corresponding to a $k^{th}$ ULM image which is immediately preceding the $(k+1)^{th}$ ULM image.

In one embodiment, the $k^{th}$ ULM image and the $(k+1)^{th}$ ULM image are immediately adjacent in the temporal dimension. The respective stacks of images are immediately adjacent in the temporal dimension. In other words, all images of the stack of images corresponding to the $(k+1)^{th}$ ULM image have a time position superior to that of the images of the stack of images corresponding to the $k^{th}$ ULM image.

In another example as illustrated in FIG. 4, the temporal series of successive ULM images comprises $N_t$ ULM images. Each of the $N_t$ ULM images is associated with a time position. That is, a $k^{th}$ ULM image of the series of successive ULM images, where $1 \le k \le N_t$, is associated with a time position referred as $t_k$. The $k^{th}$ ULM image of the series of successive ULM images is hereinafter labeled as $M(t_k)$. $M(t_k)$ may be computed based on a subset $S_{Fk}$ of a set $S_F$ comprising the $N_F$ filtered images. The subset $S_{Fk}$ may comprise $N_{Fk}$ filtered images among the $N_F$ filtered images, with $N_{Fk} < N_F$. For instance, the subset $S_{Fk}$ may comprise the filtered images of the set $S_F$ whose time positions are comprised in a temporal window of a length W and centered in $t_k$ as exemplified in FIG. 4. Further, the temporal step between two successive time positions, $t_{k-1}$ and $t_k$, $2 \le k \le N_t$, may be constant. In this case, the successive ULM images of the temporal series of ULM images may be obtained from stacks of images that at least partially overlap in the temporal dimension depending on the temporal step between two successive time positions. If $W \ge t_k - t_{k-1}$, $M(t_k)$ and $M(t_{k-1})$ may be computed from stacks of images that at least partially overlap in the temporal dimension since the last filtered image used for computing $M(t_{k-1})$ may have a time position $t_{k-1}$ superior or equal to $(t_{k-1}+t_k)/2$ and the first filtered image used for computing $M(t_k)$ may have a time position $t_k$ inferior or equal to $(t_{k-1}+t_k)/2$ ($\le t_{k-1}$). In other words, in the example of FIG. 4, the successive ULM images of the temporal series are obtained based on a temporal sliding window of the filtered images. In this case, the number $N_t$ of ULM images may be described by [Math. 1], where $Acq_t$ is the acquisition duration for the whole dataset and $Step_t$ is a sliding step of the temporal sliding window, i.e $Step_t = t_k - t_{k-1}$. The length of the temporal sliding window W, which may correspond to the recording period for an ULM image $M(t_k)$, may be superior to a period of a cardiac cycle and inferior to a minute. For example, the length of the temporal window W may be comprised between 1 s and 20 s, for instance between 1 s and 5 s. The sliding step of the temporal sliding window $Step_t$ may be comprised between 500 ms and 1 s. For instance, a sliding window with a temporal window W of 5 s and a sliding step $Step_t$ of 1 s may be used.

$$N_t = \frac{Acq_t}{Step_t} \qquad \text{[Math. 1]}$$

Therefore, each pixel of the ULM image $M(t_k)$, $1 \le k \le N_t$, may have a value corresponding to a dynamics parameter which may be a number of ultrasound contrast agents detected in the pixel during the temporal window W or a mean velocity of ultrasound contrast agents detected in the pixel during the temporal window W.

Based on the temporal series of ULM images, a measure of an evolution of the values of the at least one vascular dynamics parameter in response to the dynamical event may be computed.

3D ULM temporal matrices, generically noted $M(x,z,t)$, may be computed based on the successive ULM images of the temporal series. 3D ULM temporal matrices may be matrices of dimensions $(N_x, N_z, N_t)$, where $(N_x, N_z)$ may correspond to spatial dimensions of each ULM image. It is noted that $M(x,z,t_k)$ and $MB(t_k)$ represent the same $k^{th}$ ULM image.

The at least one vascular dynamics parameter may be chosen in the group comprising: blood flow, blood velocity, blood volume, blood pressure, vascular vessels' diameters, and any combination thereof.

A first kind of 3D ULM temporal matrix $M(x,z,t)$ may be a 3D count matrix, specifically noted $MB(x,z,t)$, and may be computed based on successive ULM count images of the temporal series. Therefore, each pixel $MB(x,z,t_k)$, with $1 \le x \le N_x$, $1 \le x \le N_z$ and $1 \le k \le N_t$, may have a value corresponding to a number of ultrasound contrast agents detected in the pixel $(x,z)$ during the temporal window W.

A second kind of 3D ULM temporal matrix $M(x,z,t)$ may be a 3D flow matrix, specifically noted $MB_F(x,z,t)$. The 3D flow matrix $MB_F(x,z,t)$ may correspond to the 3D count matrix divided by the sliding window length to get an ultrasound contrast agents flux value. That is, $$MB_F(x, z, t) = \frac{1}{W} MB(x, z, t).$$

Based on the 3D flow matrix, the evolution of the ULM contrast agents' flow during the recording of the temporal series may be measured. The blood flow may be derived since the ULM contrast agents' flow is driven by the blood flow. In particular, the ULM contrast agents' flow may be equal to the blood flow.

A third kind of 3D ULM temporal matrix $M(x,z,t)$ may be a 3D velocity matrix, specifically noted $V(x,z,t)$, and may be computed based on successive ULM velocity images of the temporal series. Therefore, each pixel $V(x,z,t_k)$, with $1 \le x \le N_x$, $1 \le x \le N_z$ and $1 \le k \le N_t$, may have a value corresponding to a mean velocity of ultrasound contrast agents detected in the pixel $(x,z)$ during the temporal window W. Based on the 3D velocity matrix, the evolution of the ULM contrast agents' velocity during the recording of the temporal series may be measured. The blood velocity may be derived since the ULM contrast agents' velocity is driven by the blood velocity. In particular, the ULM contrast agents' velocity may be equal to the blood velocity.

Likewise, a 3D blood volume matrix may be computed based on which the evolution of the blood volume during the recording of the temporal series may be measured. A 3D blood pressure matrix may also be computed based on which the evolution of the blood pressure during the recording of the temporal series may be measured.

The 3D ULM temporal matrices M(x,z,t) provide a 3D measure of the evolution of the at least one vascular dynamics parameter in response to the dynamical event. Additionally, the 3D ULM temporal matrices M(x,z,t) allow to compute two-dimensional (2D) and one-dimensional (1D) measures of an evolution of the at least one vascular dynamics parameter in response to the dynamical event. For instance, for a given pixel $(x_p, y_p)$, a temporal function $t{\rightarrow}M(x_p,z_p,t)$ may provide a measure of the evolution of the number of ultrasound contrast agents passing through the pixel $(x_p, y_p)$ over time.

In the example of FIG. 4, the measure of the evolution of the vascular dynamics parameter may a temporal ULM response P(t) in the region. The temporal ULM response P(t) may be computed based on a 3D ULM temporal matrix M(x,z,t). The temporal ULM response $P(t_k)$ may be, for each time position $t_k$, a sum of the pixel values $M(x,z,t_k)$ along the two spatial dimensions of the region as described in [Math. 2].

$$\forall k \in [1, N_t], P(t_k) = \sum_{x=1}^{N_x}\sum_{z=1}^{N_z} M(x, z, t_k) \qquad \text{[Math. 2]}$$

Alternatively, the temporal ULM response $P(t_k)$ may be, for each time position $t_k$, an average of the pixel values $M(x,z,t_k)$ along the two spatial dimensions of the region as described in [Math. 3].

$$\forall k \in [1, N_t], P(t_k) = \frac{1}{N_x \times N_y}\sum_{x=1}^{N_x}\sum_{z=1}^{N_z} M(x, z, t_k) \qquad \text{[Math. 3]}$$

In both cases, the temporal ULM response P(t) may be normalized by a value of a baseline to get relative variations. The value of the baseline may be an average value of the dynamics parameter when no dynamical event is occurring.

In some embodiments, the computation of the measure of the evolution of the at least one vascular dynamics parameter in response to the dynamical event comprises a temporal sliding average of the temporal series of ULM images. Advantageously, computing the measure of the evolution of the at least one vascular dynamics parameter in response to the dynamical event using a temporal sliding average of the temporal series of ULM images does not require a knowledge of the dynamical event's temporal pattern A(t), which may be used to analyze epileptic seizures, spreading depressions or spontaneous activities.

In some embodiments, the measure of the evolution of the at least one vascular dynamics parameter in response to the dynamical event may be an activation map.

Activation maps, noted AM(x,z), may be computed using correlation analysis, when the dynamical event's temporal pattern A(t) is known, or using SVD as described. Other processing analyses, such as PCA, may also be used by adapting the described method to said processing analyses.

Values of the pixels of the activation map AM(x,z), $1{\leq}x{\leq}N_x$, $1{\leq}x{\leq}N_z$, may be equal to a Pearson's product-moment correlation coefficient c(x,z) between the dynamical event's temporal pattern, noted A(t), and the value of M(x,z,t) as described in [Math. 4].

$$\forall (x, z), AM(x, z) = c(x, z) = \qquad \text{[Math. 4]}$$

$$\frac{\sum_{k=1}^{N_t}(M(x, z, t_k) - \overline{M(x, z)}) * (A(t_k) - \overline{A})}{\sqrt{\sum_{k=1}^{N_t}(M(x, z, t_k) - \overline{M(x, z)})^2} * \sqrt{\sum_{k=1}^{N_t}(A(t_k) - \overline{A})^2}}$$

$$\text{where } \overline{M(x, z)} = \frac{1}{N_t}\sum_{k=1}^{N_t} M(x, z, t_k) \text{ and } \overline{A} = \frac{1}{N_t}\sum_{k=1}^{N_t} A(t_k).$$

Alternatively, a SVD may be applied to the 3D ULM temporal matrix M(x,z,t) to obtain the measure of the evolution of the at the least one vascular dynamics parameter associated with the 3D ULM temporal matrix.

More specifically, SVD may be applied to a reshaped ULM Casorati Matrix, noted $\tilde{M}(x, z, t)$, of size $(N_x*N_z, N_t)$ or eventually on a reshaped M(x,z,t) matrix of size $(N_x*N_z, N_t)$. The SVD may result in the decomposition of [Math. 5], which is a decomposition based on covariance.

$$\tilde{M}(x, z, t) = \sum_{i=1}^{N_t}\lambda_i U_i(x, z)V_i(t) \qquad \text{[Math. 5]}$$

with $\lambda_i$ being a singular value, $U_i$ of size (Nx*Nz, Nx*Nz) a spatial singular vector associated to $\lambda_i$, and $V_i$ of size $(N_t*N_t)$ a temporal singular vector associated to $\lambda_i$.

The spatial singular vector Ui and the temporal singular vector $V_i$ correspond to eigenvectors of a covariance matrix $\tilde{M}$. $\tilde{M}*$ and $\tilde{M}*\tilde{M}$. This decomposition can be seen as a sum of images (each one corresponding to one $U_i$) independently modulated by the temporal signal $V_i$. Every pixel from the image $U_i$ behaves with the temporal fluctuations given by $V_i$. That is, each spatial singular vector $U_i$ may traduce a spatial response of the region to a dynamical event described by the temporal singular vector $V_i$. Further, the present inventors determined that a spatial activation singular vector $U_{i,a}$ may correspond to the region activation to the dynamical event modeled by a temporal activation singular vector $V_{i,a}$, which may then be considered as the measure of the evolution of the at least one vascular dynamics parameter in response to the dynamical event.

For a known dynamical event's temporal pattern A(t), the corresponding temporal activation singular vector $V_{i,a}$ may be determined. For each temporal singular vector $V_i$, a scalar product $p_i$ between the dynamical event's temporal pattern A(t) and the temporal singular vector $V_i$ may be computed as described in [Math. 6].

$$p_i = \frac{A(t) - \overline{A}}{\sqrt{\sum_{k=1}^{N_t}(A(t_k) - \overline{A})^2}} \cdot V_i(t) \qquad \text{[Math. 6]}$$

15

The temporal activation singular vector $V_{i,a}$ may be determined as the singular vector having the highest value of the scalar product, that is $V_{i,a}$ may be described by [Math. 7].

$$V_{i,a} = \mathrm{argmax}_{(Vi,i \in [1,N_t])} p_i \qquad \text{[Math. 7]}$$

In some embodiments, 3D ULM temporal matrices of at least one area of interest (AOI) included in the at least one region, noted $M_{AOI}(x,z,t)$ may be generated by extracting of the 3D temporal matrices $M(x,z,t)$ the pixels comprised in the AOI. The AOI may be equal to the region. Alternatively, the AOI may be smaller than the region. The AOI may be determined manually or automatically. For instance, the AOI may be automatically determined based on the values of the 3D temporal matrices $M(x,z,t)$. The AOI may be an area of the region for which the values $M(x,z,t)$ exhibit high temporal variations in response to the dynamical event compared to other areas of the region. In particular, the AOI may be chosen among a group of arterioles, venules, intra-parenchymal vessels and pial vessels. For a spontaneous activity of the nervous system, the AOI may be chosen depending on the functional connections to be studied. In particular, the AOI may be an entire brain slice (for 2D imaging) or the whole brain (for 3D imaging). For a dynamical event corresponding to a stimulus, the AOI may be chosen depending on the stimulus. For instance, for a whisker stimulus in rodents, the AOI may be a barrel field (S1BF) and/or a ventro-posterio-median (VPM) thalamic nucleus. For a visual stimulus, the AOI may be a Superior Colliculus (SC). For each AOI, the corresponding 3D ULM temporal matrices of the AOI may be matrices of dimensions $(N_{AOIx}, N_{AOIy}, N_t)$, where $(N_{AOIx}, N_{AOIy})$ may correspond to spatial dimensions of the AOI, where $N_{AOIx}$ may be equal to $N_{AOIy}$. The measures of the evolution of the at least one vascular dynamics parameter in the at least one area of interest (AOI) of the region may be computed by adapting the methods described above for measuring of the evolution of the at least one vascular dynamics parameter in the region.

Figure 5:
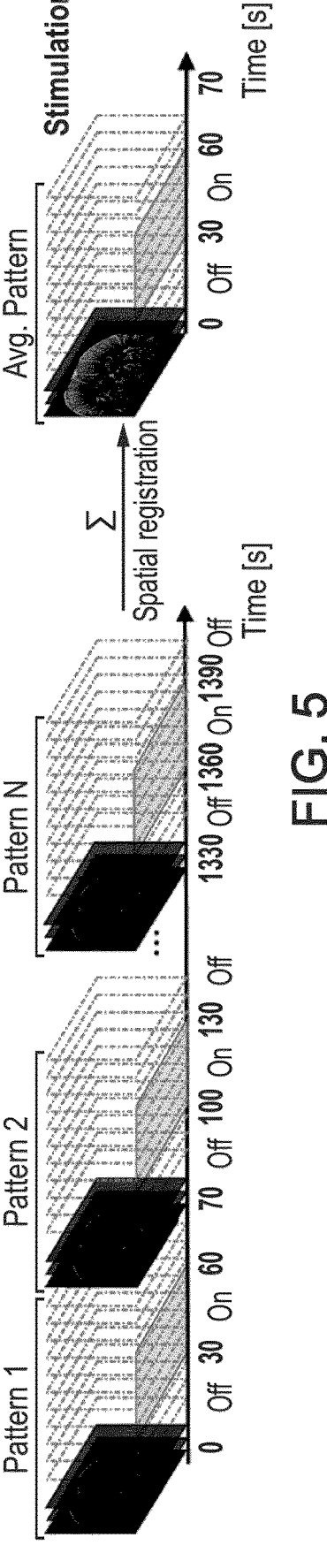
FIG. 5 illustrates a possible method of computing at least a measure of an evolution of at least one vascular dynamics parameter in response to a dynamical event according to an embodiment of the present invention.

In the example of FIG. 5, a stimulus pattern may be repeated regularly during the recording period of the temporal series of ULM images. The number N of trials may be comprised between 2 and 100, for instance comprised between 5 and 30, in particular 20.

The stimulus pattern may comprise an initial period without stimulus (i.e a baseline period) of for instance 30 s and a final period without stimulus of for instance 10 s, in the example of FIG. 4. The stimulus pattern may comprise a stimulation period with stimulus of for example 30 s in the example of FIG. 4. Other stimulus patterns, such as patterns comprising a stimulation period of 5 s may be used. The stimulus may be a task-evoked stimulus such as a visual stimulation. In rodents, the stimulus may be a whisker stimulation.

As shown in FIG. 4, equivalent time points of the N trials may be combined to obtain an average pattern. In other words, the ULM images corresponding to equivalent images may be summed. A spatial registration may be used to correct the possible motion drifts. In this case, the 3D pattern-averaged temporal matrix may have a temporal dimension of $N^s_t$, where $N^s_t$ is a number of time points in the pattern. In some embodiments, $$N^s_t = \frac{\mathrm{Pattern}_t}{\mathrm{Step}_t}.$$

16

The measures of the evolution of the at least one vascular dynamics parameter in response to the dynamical event previously described may be applied.

In particular, based on the SVD, an activation map, $AM_{SVD}(x,z)$, quantifying the ultrasound contrast agents' variation during the stimulus pattern may be computed as shown in [Math. 8].

$$\forall (x, z), AM_{SVD}(x, z) = \lambda_{ia} * U_{i,a}(x, z) * \left( \int^{t \leq stim} V_{i,a}(t)dt - \int^{t \in baseline} V_{i,a}(t)dt \right) \qquad \text{[Math. 8]}$$

Further, relative increase maps, $AM^R_{SVD}(x,z)$ may be computed as described in [Math. 9].

$$AM^R_{SVD}(x, z) = \frac{\lambda_{ia} * U_{i,a}(x, z) * \left( \int^{t \in stim} V_{i,a}(t)dt - \int^{t \in baseline} V_{i,a}(t)dt \right)}{\sum_{i=1}^{i < i_a} \lambda_i * U_i(x, z) * \int^{t \in baseline} V_i(t)dt} \qquad \text{[Math. 9]}$$

Alternatively, the N trials may not be averaged, in which case the 3D temporal matrix may have a temporal dimension of $N*N^s_t$.

In particular, based on the SVD, an activation map for the non-averaged data, $AM_{SVD}(x,z)$, quantifying the ultrasound contrast agents' variation during the stimulus pattern may be computed as shown in [Math. 10].

$$\forall (x, z), AM_{SVD}(x, z) = \sum_{k=1}^{Nstim} \lambda_{ia} * U_{i,a}(x, z) * \left( \int^{t \leq stim_k} V_{i,a}(t)dt - \int^{t \in baseline_k} V_{i,a}(t)dt \right) \qquad \text{[Math. 10]}$$

Figure 6:
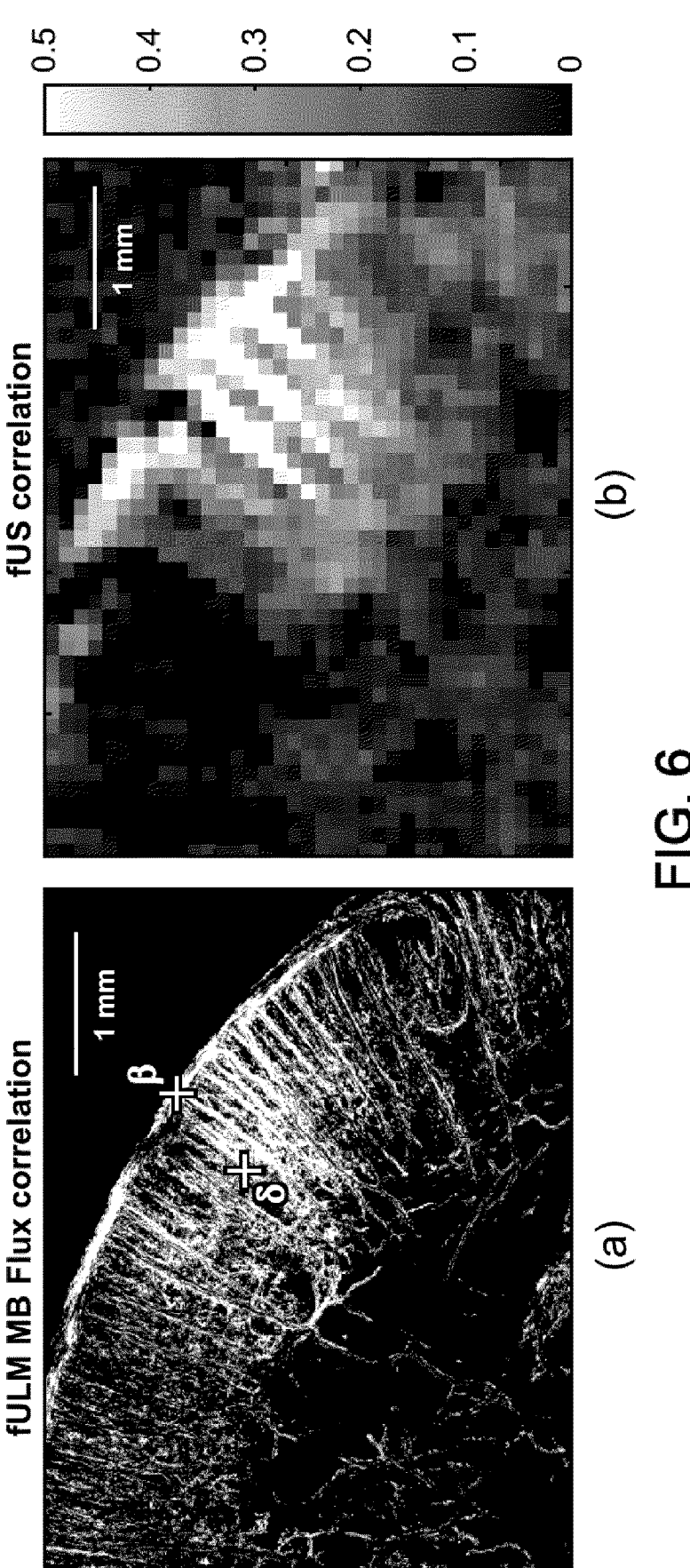
FIG. 6(*a*) shows an example of a measure (activation map) of an evolution of at least one vascular dynamics parameter in response to a dynamical event in a rat obtained with a method of the present disclosure.

As shown in FIG. 6(a), a map of functional hyperaemia in cortical and subcortical areas at a 6.5 μm resolution may be obtained with a method of the disclosure based on the Pearson correlation between the pattern-averaged temporal ULM matrix and the stimulation paradigm. In particular, in the example of FIG. 6(a), vascular activity in a pial vessel β and a smaller blood vessel δ, which is a first order branching after descending an arteriole, may be obtained. A functional Ultrasound (fUS) imaging experiment, shown on FIG. 6(b), confirms brain activation in the same region. In this example, the spatial resolution obtained with the method of the present disclosure, which may be named functional Ultrasound Localization Microscopy (fULM), is 16-fold better than that achieved with the fUS imaging experiment.

Figure 7A:
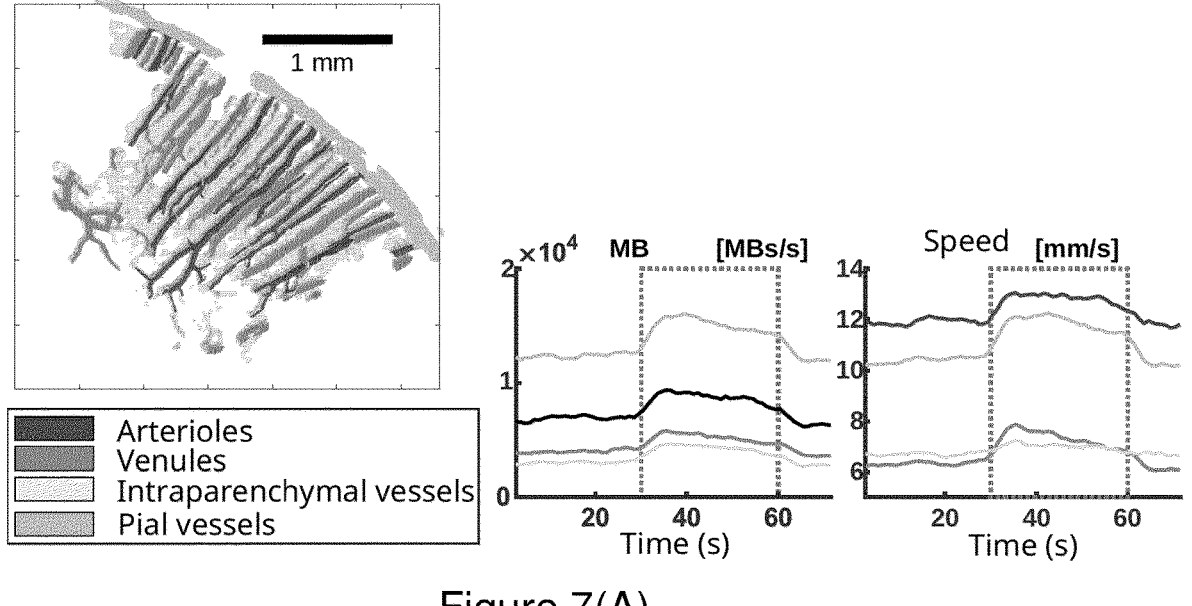
FIG. 7(*a*) illustrates an example of a functional Ulm map showing a segmentation of the activated barrel cortex (S1BF) into four vascular compartments: penetrating arterioles, venules, pial vessels and intraparenchymal vessels.
Figure 7B:
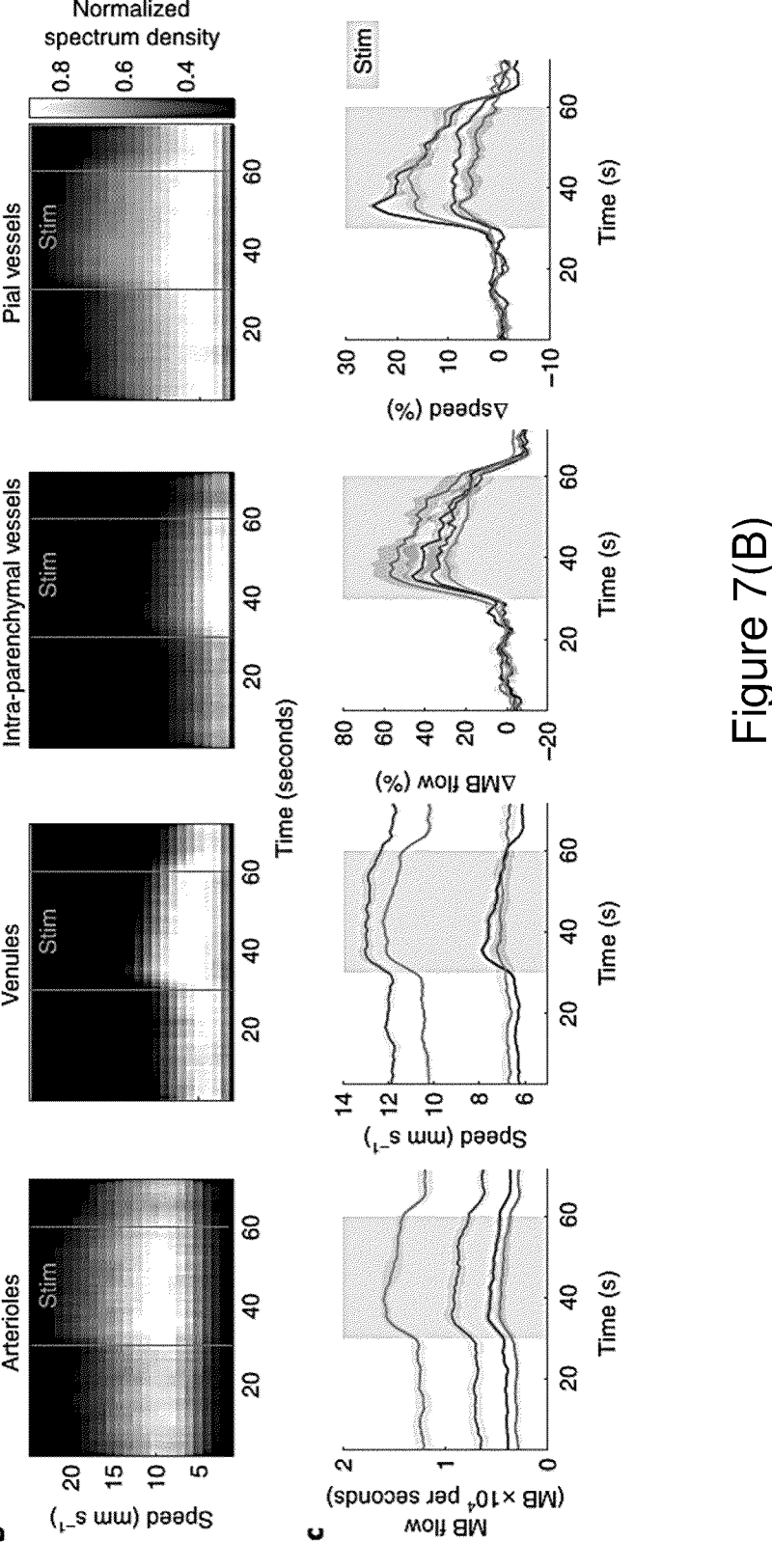

Thanks to the microscopic resolution, the functional Ultrasound Localization Microscopy of the present disclosure may be used to measure the dynamic parameters such as microbubbles flow, speed, and vessel diameters in different vascular compartments. FIG. 7(A) shows a segmentation of the barrel cortex (S1BF) into four vascular compartments:

penetrating arterioles, venules, pial vessels and intraparenchymal vessels based on the functional ULM maps. FIG. 7(B) shows the dynamic histograms of microbubbles velocities as well as microbubbles flow and velocity time courses. These results reveal the highest relative increase in microbubbles flow during activation in intraparenchymal vessels compared to larger vessels such as penetrating arterioles or pial arterioles, confirming that these intraparenchymal vessels are the most important contributors to the neurovascular coupling. Thus, the functional UM images enable the quantification of the contributions of different vascular compartments.

Owing to the performances of the method of the present disclosure, the computing module 3 of the apparatus 1 of FIG. 1 may adapted to estimate a seizure focus based on the measure of the evolution of the at least one vascular dynamics parameter in response to the dynamical event obtained by the method of the present disclosure. For instance, based on the values of evolution of the flow and/or the velocity associated with the pixels of the region during an epileptic seizure, a spreading depression respectively, the seizure focus, the spreading depression origin respectively, from which originates the activity may be located.

Additionally, the computing module 3 may be adapted to diagnosticate whether the measure of the evolution of the at least one vascular dynamics parameter in response to the dynamical event corresponds to a predetermined disease, in particular a neurodegenerative disease.

For determining whether the measure of the evolution of the at least one vascular dynamics parameter in response to the dynamical event is normal and/or whether the measure of the evolution of the at least one vascular dynamics parameter in response to the dynamical event corresponds to a predetermined disease, computing module 3 may compare said parameters to predetermined thresholds.

In a variant, for determining whether the measure of the evolution of the at least one vascular dynamics parameter in response to the dynamical event is normal and/or whether the measure of the evolution of the at least one vascular dynamics parameter in response to the dynamical event corresponds to a predetermined disease, computing module 3 may use a neural network trained to determine whether the measure of the evolution of the at least one vascular dynamics parameter in response to the dynamical event is normal and/or to determine whether the measure of the evolution of the at least one vascular dynamics parameter in response to the dynamical event corresponds to a predetermined disease.

The apparatus 1 may also be used to monitor efficiency of a medical treatment against a predetermined disease, in particular a disease among epilepsy, spreading depression, and a neurodegenerative disease, based on the measure of the evolution of the at least one vascular dynamics parameter in response to the dynamical event. To this end, the measure of the evolution of the at least one vascular dynamics parameter in response to the dynamical event may be measured at different points of time at least before and after the medical treatment, possibly including during the medical treatment, to determine whether the medical treatment reduces seizures and/or improves neurovascular coupling.

In the present examples, the vascular network described is the vascular network of a nervous system. Nevertheless, the methods and apparatuses described may be adapted to any vascular network.

The invention claimed is:

1. Method for imaging vascular activity dynamically at a microscopic scale in a vascular network of an organ of a human or animal, and the organ including one more isolated ultrasound contrast agents injected by an ultrasound agent injection device, the method including:

(a) performing by a computing module a temporal series of Ultrasound Localization Microscopy, ULM, images of at least one region of the vascular network from a set of raw data acquired by an array of ultrasonic transducers, to obtain values of at least one vascular dynamics parameter in at least one area of interest in the at least one region during a recording period, the temporal series of ULM images being constructed from a temporal series of images of the region, each ULM image being constructed from a stack of images of the temporal series of images, at least some of the images of a stack of images corresponding to a $(k+1)^{th}$ ULM image having a time position superior to that of the images of a stack of images corresponding to a $k^{th}$ ULM image which is immediately preceding the $(k+1)^{th}$ ULM image, said recording period of the temporal series of ULM images including at least one dynamic event, due to a cause other than cardiac pulsatility, the at least one dynamic event activating a change in a local hemodynamics and/or a change in a structural conformation of the vascular network in the at least one region thereof;

(b) computing by the computing module, based on the values of the at least one vascular dynamics parameter from the temporal series of ULM images, a measure of an evolution of the at least one vascular dynamics parameter in response to the at least one dynamic event.

2. Method according to claim 1, wherein each image of the temporal series of images is constructed from successive compound images.

3. Method according to claim 1, wherein a recording period of an ULM image is superior to a period of a cardiac cycle and inferior to a minute.

4. Method according to claim 1, wherein the vascular network is a vascular network of a nervous system and the at least one dynamic event is a stimulus delivered to the nervous system, the method further including:

(c) delivering the at least one stimulus to the nervous system.

5. Method according to claim 1, wherein the vascular network is a vascular network of a nervous system and the at least one dynamic event is a spontaneous activity of the nervous system.

6. Method according to claim 4, wherein steps (a) and (c) are repeated for N trials and the measure of the evolution of the at the least one vascular dynamics parameter is computed based on the temporal series of the N trials, wherein N is an integer larger than 1.

7. Method according to claim 4, wherein computation of the measure of the evolution of the at least one vascular dynamics parameter in response to the at least one dynamic event comprises a correlation between the at least one stimulus and the temporal series of ULM images.

8. Method according to claim 1, wherein computation of the measure of the evolution of the at least one vascular dynamics parameter in response to the at least one dynamic event comprises a Singular Value Decomposition, SVD, and/or a Principal Component Analysis, PCA, of the temporal series of ULM images.

9. Method according to claim 1, wherein computation of the measure of the evolution of the at least one vascular dynamics parameter in response to the at least one dynamic event comprises a sliding average of the temporal series of ULM images.

10. Method according to claim 1, wherein successive ULM images of the temporal series of ULM images are obtained from stacks of images that at least partially temporally overlap.

11. Method according to claim 1, wherein the at least one vascular dynamics parameter is chosen from the group consisting of: blood flow, blood velocity, blood volume, blood pressure, vascular vessels' diameters, and any combination thereof.

12. Method according to claim 1, wherein said at least one region is segmented in at least one vascular compartment.

13. Method according to claim 12, wherein said at least one area of interest of the at least one region corresponds to one of said at least one vascular compartments.

14. Method according to claim 1, wherein successive ULM images of the temporal series of ULM images are obtained from respective stacks of images that are successive in the temporal dimension.

15. Method according to claim 14, wherein said respective stacks of images are immediately adjacent in the temporal dimension.

16. Apparatus for imaging vascular activity dynamically at a microscopic scale in a vascular network of a human or animal, the apparatus including:

(a) an ultrasound contrast agent injection device and an ultrasound measuring device adapted to perform a temporal series of Ultrasound Localization Microscopy, ULM, images of at least one region of the vascular network, to obtain values of at least one vascular dynamics parameter in at least one area of interest in the at least one region during a recording period, the temporal series of ULM images being constructed from a temporal series of images of the region, each ULM image being constructed from a stack of images of the temporal series of images, at least some of the images of a stack of images corresponding to a $(k+1)^{th}$ ULM image having a time position superior to that of the images of a stack of images corresponding to a $k^{th}$ ULM image which is immediately preceding the $(k+1)^{th}$ ULM image, said recording period of the temporal series of ULM images including at least one dynamic event, due to a cause other than cardiac pulsatility, the dynamic event activating a change in a local hemodynamics and/or change in a structural conformation of the vascular network in the at least one region thereof;

(b) a computing module adapted to compute, based on the values of the at least one vascular dynamics parameter from the temporal series of ULM images, a measure of an evolution of the at least one vascular dynamics parameter in response to the at least one dynamic event.

17. Apparatus according to claim 16, wherein the at least one dynamic event is an epileptic seizure or a spreading depression and the computing module is adapted to estimate a seizure focus location or a spreading depression origin from the measure of the evolution of the at least one vascular dynamics parameter in response to the epileptic seizure or the spreading depression.

18. Apparatus according to claim 16, wherein the computing module is adapted to diagnose whether the measure of the evolution of the at least one vascular dynamics parameter in response to the at least one dynamic event corresponds to a predetermined disease.

19. Apparatus according to claim 16, wherein the computing device is adapted to monitor efficiency of a medical treatment against a predetermined disease selected from the group consisting of: epilepsy, spreading depression, and a neurodegenerative disease, based on the measure of the evolution of the at least one vascular dynamics parameter in response to the at least one dynamic event.

20. Computer-readable non-transient recording medium on which a software is registered to implement a method according to claim 1 when the software is executed by a processor.

21. Computer software comprising instructions to implement the method according to claim 1 when the software is executed by a processor.

* * * * *